United States Patent
Van Der Leden

(10) Patent No.: US 7,374,626 B2
(45) Date of Patent: May 20, 2008

(54) METHOD FOR BONDING A BODY SIDE WAFER OF A STOMA SYSTEM AND A FURTHER COMPONENT OF SAID STOMA SYSTEM WITH EACH OTHER

(75) Inventor: Arie Gijsbert Van Der Leden, Kapellen (BE)

(73) Assignee: Eurotec Beheer B.V., Roosendaal (NL)

( * ) Notice: Subject to any disclaimer, the term of this patent is extended or adjusted under 35 U.S.C. 154(b) by 215 days.

(21) Appl. No.: 10/866,798

(22) Filed: Jun. 15, 2004

(65) Prior Publication Data

US 2005/0277901 A1 Dec. 15, 2005

(51) Int. Cl.
*B32B 37/00* (2006.01)
(52) U.S. Cl. .................... 156/73.1; 156/580.2
(58) Field of Classification Search ........... 156/73.1, 156/308.2, 308.4, 580.1, 580.2; 264/442, 264/443, 445
See application file for complete search history.

(56) References Cited

U.S. PATENT DOCUMENTS

| | | | |
|---|---|---|---|
| 4,572,753 A | 2/1986 | Bach | |
| 4,770,730 A | 9/1988 | Abe | |
| 5,074,852 A * | 12/1991 | Castellana et al. | 604/336 |
| 5,244,520 A * | 9/1993 | Gordon et al. | 156/73.1 |
| 6,830,565 B2* | 12/2004 | Cisko, Jr. | 604/336 |

FOREIGN PATENT DOCUMENTS

| | | |
|---|---|---|
| EP | 0 435 638 A1 | 7/1991 |
| EP | 0 927 549 A1 | 7/1999 |
| GB | 1 571 657 | 7/1980 |
| JP | 58 038130 A | 3/1983 |

* cited by examiner

*Primary Examiner*—James Sells
(74) *Attorney, Agent, or Firm*—Young & Thompson

(57) ABSTRACT

A body side wafer of a stoma system is bonded to a further component thereof using an ultrasonic welding apparatus including an anvil and a horn. The horn includes a first welding surface and the anvil includes a second welding surface. At least one of the two welding surfaces includes a pattern of projections, preferably a plurality of adjacently placed conical projections such as pyramids, truncated pyramids, prismoids, cones, truncated cones or cylinders. The steps include clamping the parts to be welded between the first and second welding surface, and ultrasonically vibrating the horn with respect to the anvil. The resulting welded structure includes a first and a second welding area, respectively, which are bonded to each other by ultrasonic welding. At least one of the two welding areas includes a pattern of depressions, preferably a plurality of adjacently placed conical depressions, preferably in a goffered, honeycomb or diamond pattern.

13 Claims, 5 Drawing Sheets

US 7,374,626 B2

METHOD FOR BONDING A BODY SIDE WAFER OF A STOMA SYSTEM AND A FURTHER COMPONENT OF SAID STOMA SYSTEM WITH EACH OTHER

FIELD OF THE INVENTION

The invention relates to a method for bonding a body side wafer of a stoma system and a further component of said stoma system to each other, using an ultrasonic welding apparatus. The invention further relates to a stoma system comprising a body side wafer and a further component, wherein the body side wafer and further component comprise a first and a second welding area, respectively, which are bonded to each other by ultrasonic welding stoma systems, particularly in the United States, are also referred to as ostomy systems.

BACKGROUND OF THE INVENTION

A number of diseases involving the intestinal and urinary tracts can result in the construction of an artificial outlet on the abdominal area for stools and/or urine; this is referred to as a stoma.

A diversion of the large intestine into the abdominal wall is referred to as a colostomy. The diversion of the small intestine is referred to as an ileostomy and when urine is disposed of through an artificial opening in the abdominal wall one refers to a urostomy. Usually a stoma patient is totally dependent on a well-functioning external collection device attached to the peristomal skin.

Over the years a large variety of stoma appliances has been developed. Patients with a colostomy collect the relatively normal faeces in closed pouches which are usually changed several times a day. Patients with an ileostomy collect their relatively liquid stool in drainable pouches, the opening of which can be opened and closed with a tail clip. Patients with a urostomy collect their urine in a pouch with a drain tap. Ileostomy and urostomy pouches are usually changed once a day.

Stoma appliances can be divided into two main systems; the one-piece system and the two-piece system.

In case of a one-piece stoma system, the body side wafer, which consists of a special adhesive, is an integral part of the pouch. This type of pouch is designed to be fixed directly to the skin and has the advantage that the total surface of the adhesive layer is flat and flexible, which allows it to follow the contours of the skin easily. However, the major disadvantage of a one-piece system is that the adhesive has to be removed from the skin with every pouch change, which may cause skin irritations.

In case of a two-piece stoma system, the body side adhesive layer and the pouch are two separate components. First one attaches a special body side wafer with flange onto the skin. This flange is usually made from plastic and is circularly shaped with an upstanding or projecting rib as a coupling member. The stoma pouch is also provided with a circular coupling member which can be attached on or around the projecting rib of the body side flange. A major advantage of a two-piece stoma system is that the peristomal skin is not disturbed during pouch changes as the adhesive part stays in place. A major disadvantage of a two-piece stoma system is that the body side adhesive wafer is far less flexible and flat compared with a one-piece system because of the rigidity and the higher profile of the built-in coupling member, which makes it less suitable for stomas positioned in difficult areas such as folds and irregularities of the skin.

The design of most two-piece stoma systems is based on the two-piece stoma system designed by Steer et al. (British patent application 1,571,657). This stoma system consists of a body side wafer produced from a special hydrocolloid adhesive, covered by a thin polyethylene film, on which a circular polymeric flange with an upstanding or projecting rib has been attached which functions as a coupling member. The two-piece stoma system developed by Steer et al. is characterized by its property that all stoma appliances and stoma pouches within this system are provided with a polymeric coupling member with a circular channel, made to snap tightly over the projecting rib on the body side flanges. The projecting rib fits exactly in between the two walls of the channel in the coupling member of the stoma pouch.

Up until now various bonding techniques have been applied to attach a further component of the stoma system onto a body side wafer. For example a pouch onto the body side wafer in case of a one-piece stoma system, or a flange onto the body side wafer in case of a two-piece stoma system. These methods comprise heat sealing and gluing, using for example a double-sided adhesive or a hot-melt.

In the case of heat sealing, a further component such as the flange for example, is welded by applying heat locally on the welding area of the body side wafer. However this is not possible with the two-piece stoma system of Steer et al., since the relatively thick welding area of the flange hinders the transmission of heat to the thin film on the body side wafer. In other words, the polymeric flange would already melt and deform before the heat could reach the polymeric foam or film layer to be welded on the body side wafer.

Alternatively, the flange can be attached to the polymeric foam layer of the body side wafer by means of double-sided adhesive tape. This method, which is commonly used, consists of die-cutting circular adhesive rings from double-sided pressure sensitive adhesive tape that corresponds in size with the welding area of the flange. When such a double-sided adhesive washer is pressed together between the body side wafer and the welding area of the flange, a reliable bond can be obtained. The major disadvantage of this method is that it is a laborious intensive and expensive process.

Alternatively, the flange can be bonded to the polymeric foam layer of the body side wafer with the use of glue, usually a so-called 'hot melt'. This heat-activated glue is manually or automatically applied between the flange and the appropriate surface of the body side wafer and when the two parts are pressed together—and in case of a hot melt, after cooling down—a good bond is be obtained. The major disadvantage of this method is that manual bonding of the flange is very laborious intensive and in the case of a more automated production method the bonding process, owing to the need for accurate dosage, is very complicated and requires high investments.

It is an object of the present invention to attach a further component of the stoma system onto a body side wafer with an improved bonding.

SUMMARY OF THE INVENTION

For bonding a body side wafer of a stoma system and a further component of said stoma system to each other, the method according to the invention uses an ultrasonic welding apparatus comprising an anvil and a horn, wherein the horn comprises a first welding surface and the anvil comprises a second welding surface, wherein at least one of the first and second welding surfaces comprises a pattern of projections, preferably a plurality of adjacently placed conical projections such as pyramids, truncated pyramids, prismoids, cones, truncated cones or cylinders, wherein the method comprises the steps of clamping areas to be welded of the body side wafer and the further component between the first and second welding surface, and ultrasonically vibrate said horn with respect to said anvil. Said method results in a stoma system comprising a body side wafer and a further component, wherein the body side wafer and further component comprise respectively a first and a second welding area which are bonded to each other by ultrasonic welding, wherein at least one of said first and second welding areas comprises a pattern of depressions, preferably a plurality of adjacently placed conical depressions, preferably in a goffered, honeycomb or diamond pattern. In this way a strong and reliable bond can be obtained over the full welding area between the body side wafer and the further component so that they cannot be easily be torn apart.

Said method is particularly advantageous for the production of a two-piece stoma system wherein the body side wafer comprises a polymeric foam top layer, and wherein the flange is ultrasonically welded onto said polymeric foam layer.

In an embodiment said pattern of projections is provided on the first welding surface. Preferably the second welding surface is pressed against the body side wafer and the first welding surface is pressed against the further component. Thus the welding area of the further component, the second welding area, comprises said pattern of depressions.

In a further embodiment the body side wafer comprises a layer of polymeric foam. Preferably the layer of polymeric foam comprises Polyethylene, EVA, or a blend of these polymers. Preferably the further component is welded onto said layer of polymeric foam of the body side wafer.

In an embodiment the further component comprises a flange comprising a coupling member for coupling a stoma pouch with said flange. Preferably said flange is essentially circularly shaped with an upstanding or projecting rib as a coupling member, and said flange surrounds said aperture. Preferably the body side wafer comprises an aperture, and said flange is welded around said aperture. Preferably said horn comprises a circular first welding surface, enabling to weld said flange onto said body side flange in one go. Thus the weld of said flange completely surrounds the aperture and provides a sealing between said flange and said body side wafer, preventing any leakage between them.

The method can further produce a body side wafer for a two-piece stoma system, wherein said body side wafer comprises an aperture and an essentially circularly shaped flange surrounding said aperture, said flange comprises a coupling member for coupling a stoma pouch with said flange, and said flange is bonded onto said body side wafer by a circular welded area adjacent to said flange, which circular welded area comprises a pattern of depressions. Preferably the pattern of depressions comprises a plurality of adjacently placed depressions, which make up a goffered, honeycomb or diamond pattern.

BRIEF DESCRIPTION OF THE DRAWINGS

The present invention will become more fully understood from the detailed description given hereinbelow and the accompanying drawings, which are given by way of illustration only and wherein.

DETAILED DESCRIPTION OF PREFERRED EMBODIMENTS

Figure 1A:
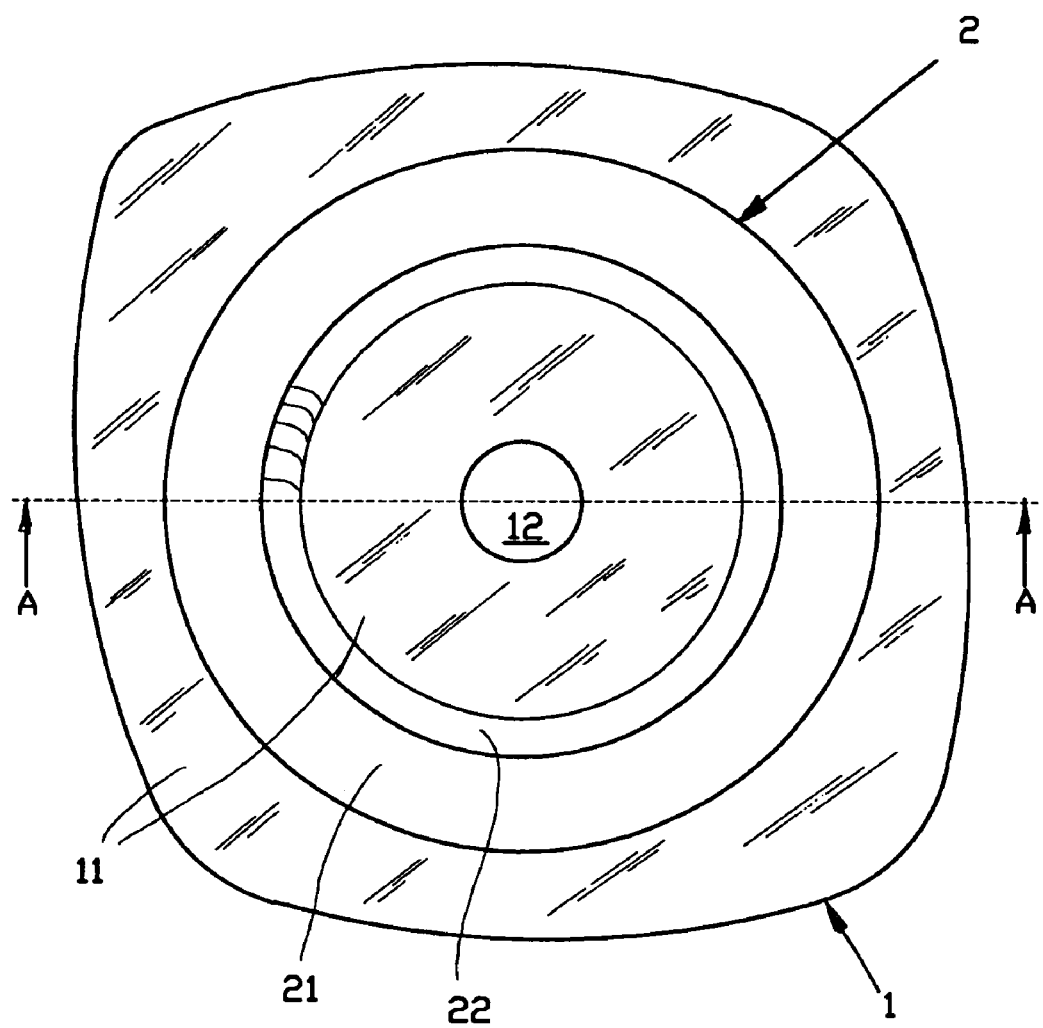
FIG. 1A shows a commonly used body side wafer of a two-piece stoma system with an integrated top layer of polyethylene film, where the welding area of the flange is welded together by using a horn with two protruding concentric circular welding profiles.
Figure 1B:
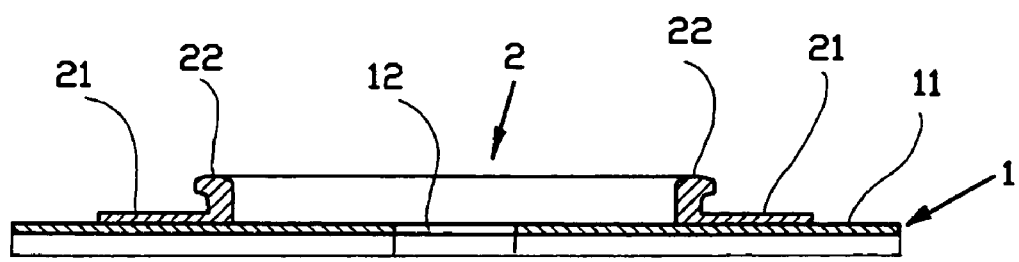
FIG. 1B shows a cross-section of the body side wafer of FIG. 1A along the line A-A.

As an example, the method according to the invention is explained hereinbelow for the production of a body side wafer 1 with a round aperture 12 of a two-piece stoma system as shown in FIGS. 1A and 1B, with an integrated top layer of polyethylene 11. A disadvantage of this polyethylene film 11 is that it makes the body side wafer 1 rigid and less flexible. An advantage of this polyethylene film 11 is that is allows easy welding of the flange 2 by means of an ultrasonic welding technique, in particular where the composition of the polymeric flange 2 is at least partly identical or chemically equivalent to the polyethylene top layer 11 of the body side wafer 1.

The flange 2 comprises a projecting rib 22 for the coupling of a stoma pouch (not shown) to the body side wafer 1. Furthermore the flange 2 is provided with an outwardly projecting sealing strip 21 for attaching the flange 2 onto the top layer 11 of the body side wafer 1, preferably by ultrasonic welding.

Ultrasonic welding is achieved by clamping the two pieces to be welded between an anvil and a horn, also called vibrating probe, which is brought into vibration by an ultrasonic transducer, also called a sonotrode. The vibration raises the temperature at the interface and produces the weld. The results of this welding process can be optimized by selecting the right combination of the frequency and amplitude of the sound waves, the welding time and the clamping force.

Because the welding area of the polymeric flange 21 is relatively thick and the polyethylene top layer 11 relatively thin, the process of ultrasonic welding is a critical process. If the mix mentioned above generates too much energy, the welding profile of the horn will burn into one or both polymeric surfaces being welded. If the mix mentioned above generates too little energy, the two parts being welded will not or not sufficiently melt together. In both cases the welding strength of the flange 2 to the surface of the body side wafer 1 will be insufficient, thus creating an unreliable product which may cause leakage and may severely impair the well-being of the end-user.

Figure 2A:
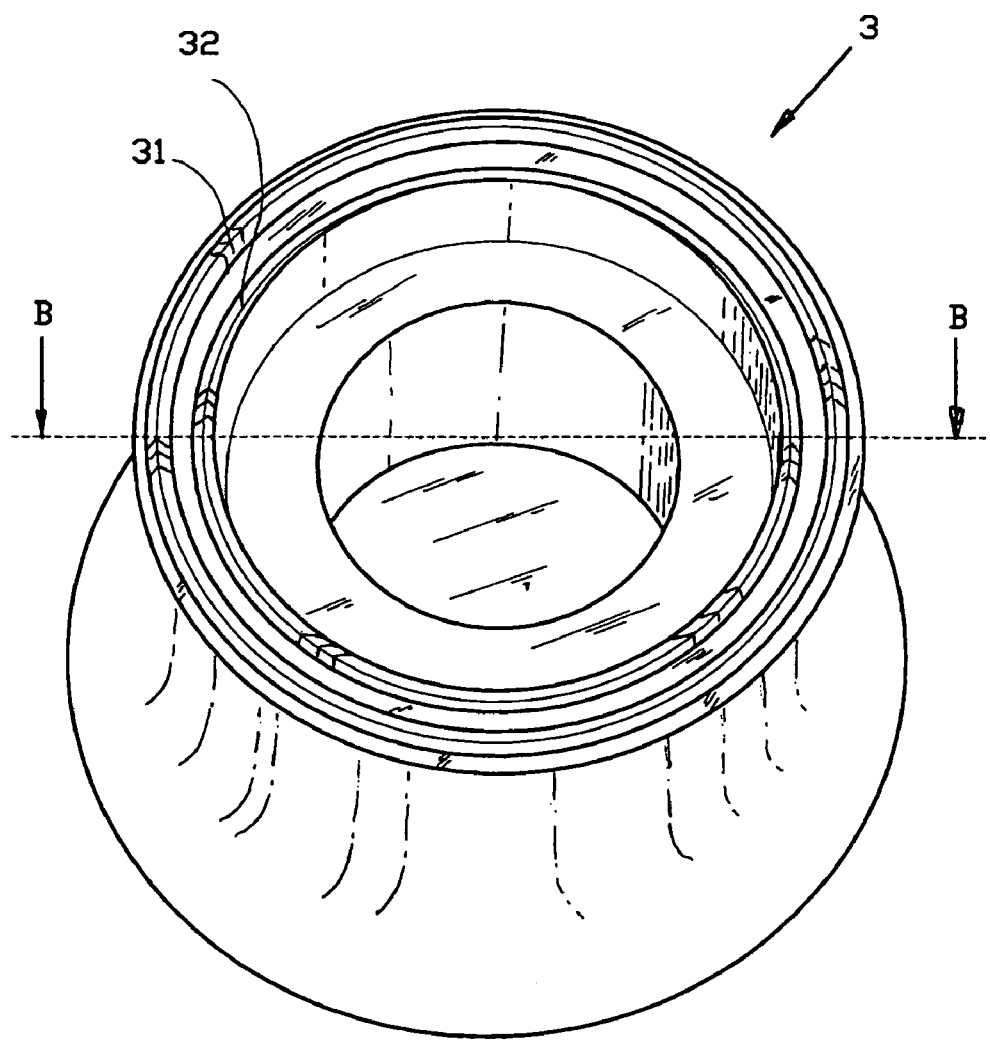
FIG. 2A shows the described welding profile of the horn according to FIG. 1.
Figure 2B:
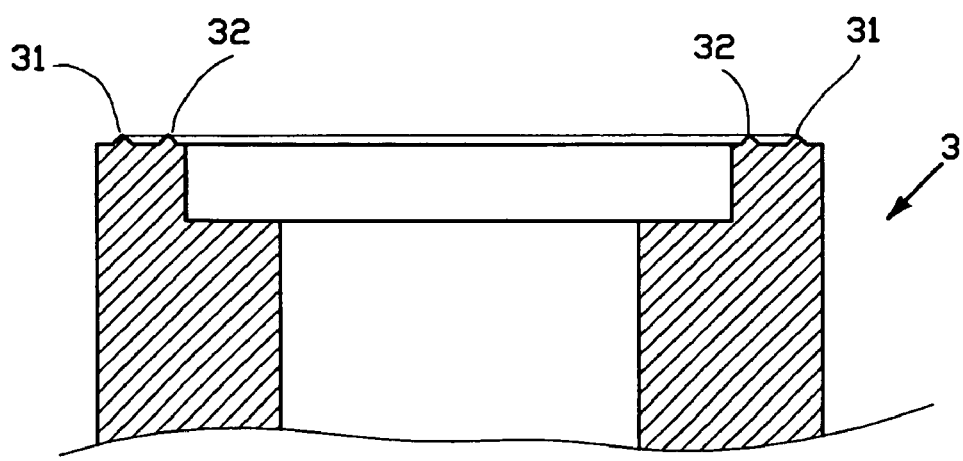
FIG. 2B shows a cross-section of the horn of FIG. 2A along the line B-B.
Figure 3:
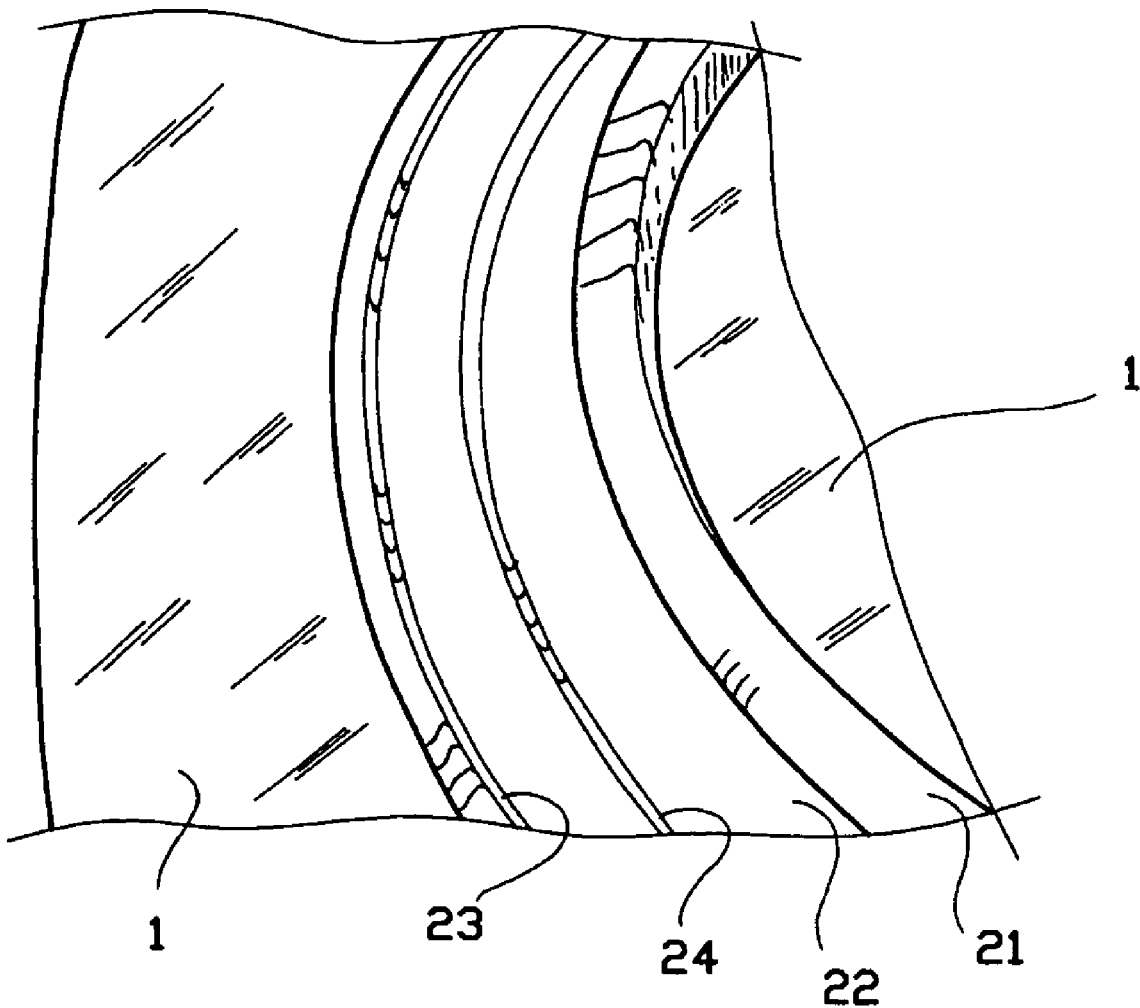
FIG. 3 shows the concentric welds of the welding area of the flange according to FIG. 1 in more detail.

As shown in FIGS. 2A and 2B, the horn 3—most commonly made from titanium or aluminum—is provided with two protruding concentric circular welding profiles 31, 32. With the correct combination of frequency and pressure, the flange 2 and the polyethylene film 11 of the body side wafer 1 are melted together at the concentric circular welds 23, 24, as shown in FIG. 3, underneath the concentric circular welding profiles 31, 32, as shown in FIG. 2B in more detail.

As described earlier, the disadvantage of the polyethylene top layer of the body side wafer of the two-piece stoma system designed by Steer et al. is that it makes the body side wafer rigid and less flexible. For this reason softer polymeric flange materials with a thinner profile were searched for on the one hand while on the other hand polymers were searched for which were able to make the body side wafer more flexible, allowing the wafer to follow the contours of the skin much better. Replacement of the smooth polyethylene film by one with a goffered structure (waffle structure) or a ribbed structure already helps to improve the flexibility of the body side wafer. The use of a top layer 11 of polymeric foam, such as polyethylene foam, also improves the flexibility of the two-piece body side wafer 1.

With the horn 3 comprising two protruding concentric circular welding profiles 31, 32, as shown in FIG. 2, the seal obtained proved to be unreliable. In particular when a relatively thick flange 2 is welded ultrasonically onto a surface 11 of polyethylene foam of the body side wafer 1, the surface of the polymeric flange 22 is melted together with the thin cell walls of the upper foam layer 11 of the body side wafer 1. This creates unsatisfactory adhesion between the flange 2 and the body side wafer 1, and the flange 2 could be torn from the body side wafer 1.

Figure 4:
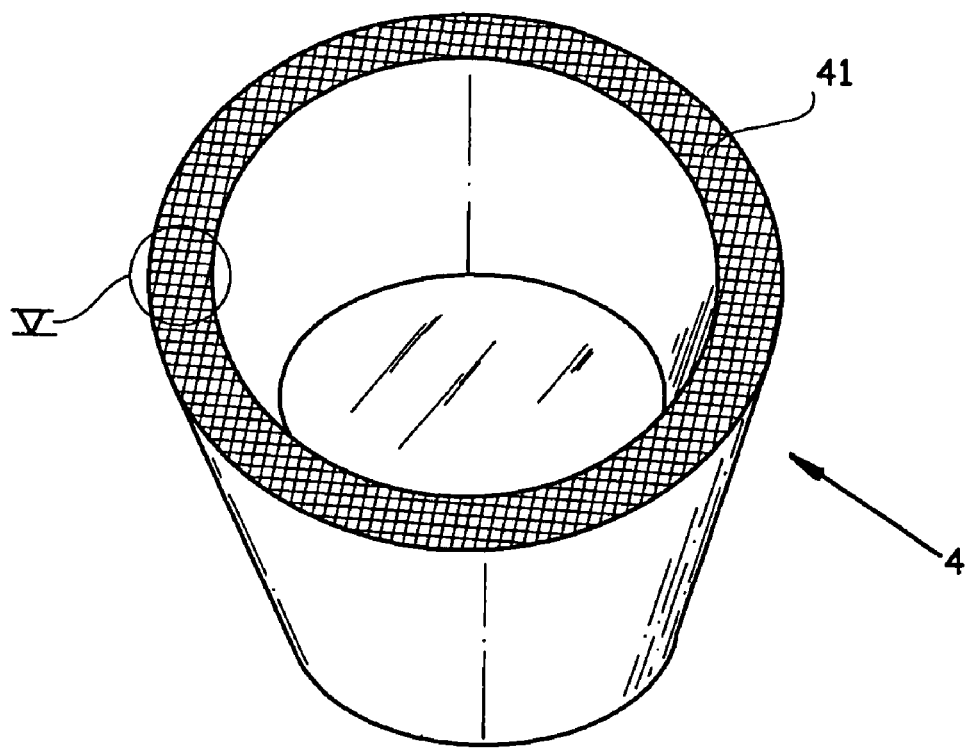
FIG. 4 shows the special horn with a pattern of quadrangular pyramid-shaped structures.
Figure 5:
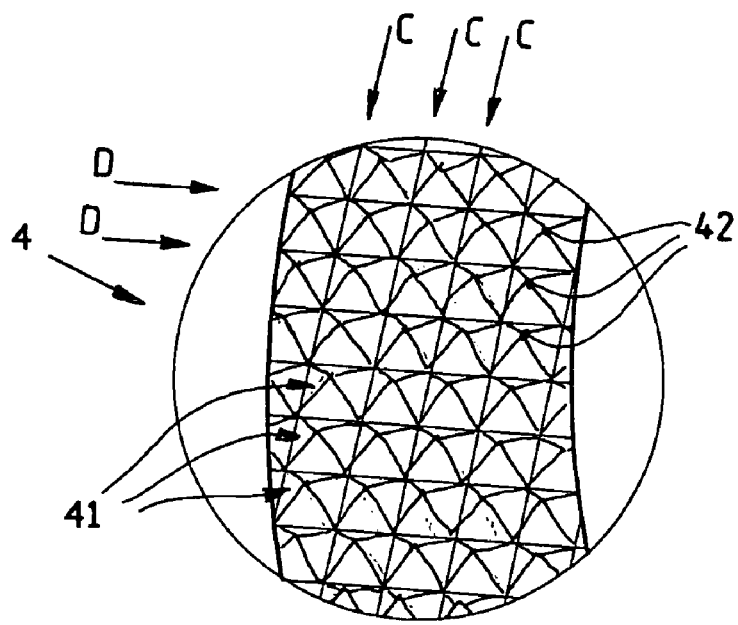
FIG. 5 shows the welding profile of the special horn according to FIG. 4 in greater detail.

In order to obtain an improved bonding between the flange 2 and the body side wafer 1, the horn 4 is provided with a welding profile comprising a pattern of conical projections, in particular a plurality of adjacently placed pyramid-shaped projections 41, as shown in FIGS. 4 and 5. In this exemplary embodiment a plurality of adjacently placed quadrangular pyramid-shaped projections 41 was chosen, because this pattern is relatively easy to mill. FIG. 5 is an enlarged view of the area V in FIG. 4 showing these quadrangular pyramid-shaped projections 41 in detail. Each of quadrangular pyramid-shaped projections 41 have a quadrangular base and a projecting top 42. This profile can be obtained by milling along the directions C and D, wherein the directions C are essentially perpendicular to the directions D.

However, the welding profile could also consist of a pattern of other facet shapes or of small convex, trapezium, conical or cylindrical shapes. For example, the welding profile may alternatively comprise triangular pyramids in a hexagonal pattern.

Figure 6:
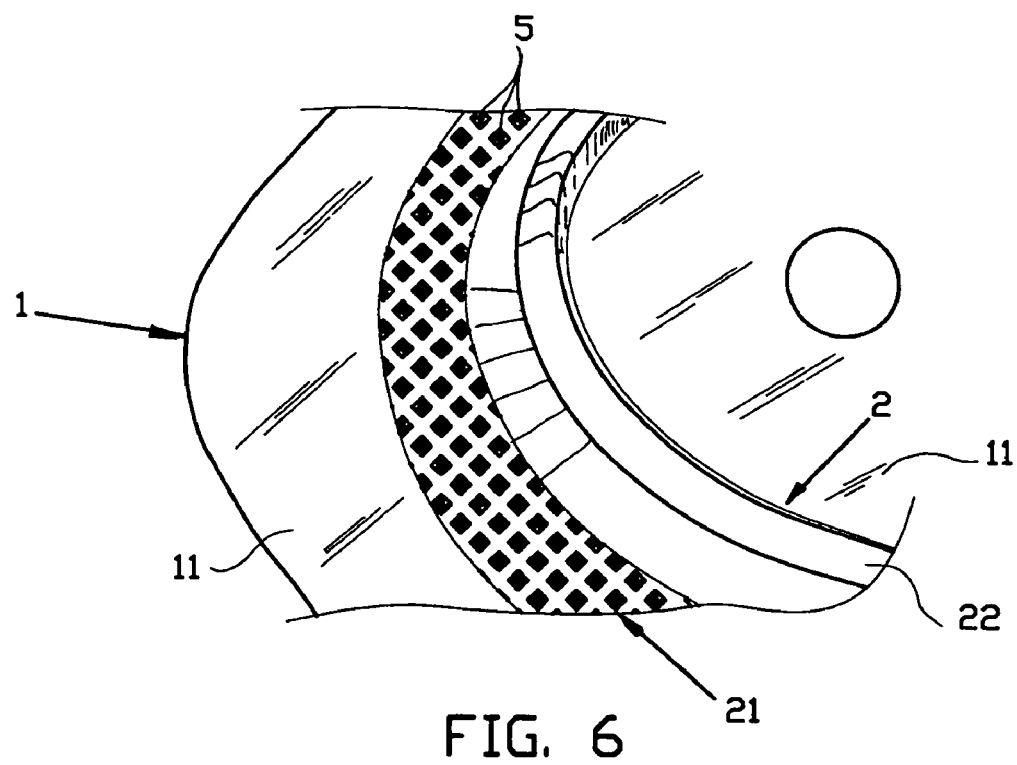
FIG. 6 shows the results of the ultrasonic welding process using the special horn according to FIG. 4.

During the ultrasonic welding, the horn 4 provided with a welding profile comprising a pattern of conical projections, in particular a plurality of adjacently placed quadrangular pyramid-shaped projections 41, is ultrasonically vibrated and pressed under a relatively high pressure (for example within a range of 70-110 PSI) into the deeper area of the polymeric foam layer 11. During this process each individual mini-pyramid 41 makes the polymeric walls of layers of foam cells located even deeper melt together according to the pattern on the welding profile of the horn 4. In this way a strong and reliable seal can be obtained over the full welding area 21 between the flange 2 and the polymeric foam layer 11 of the body side wafer 1, as shown in FIG. 6.

Due to the pattern of conical projections 41, the welding area 21 of the coupling member or flange 2 shows a regular pattern of depressions 5 or mini-dents on the position where the flange material has been pressed into the foam layer by the pattern of conical projections 41. In this exemplary embodiment the welding area 21 comprises a plurality of adjacently placed quadrangular depressions 5, which make up a goffered pattern as shown in FIG. 6.

Figure 7:
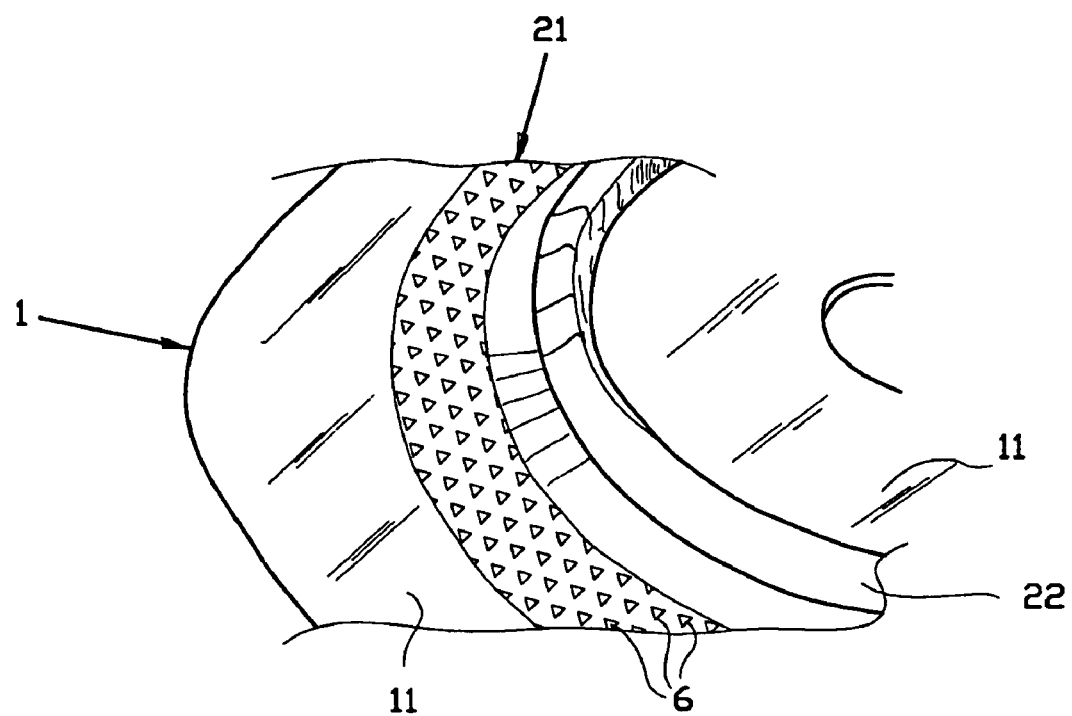
FIG. 7 shows the results of the ultrasonic welding process using an alternative horn with triangular pyramids in a hexagonal pattern.

In an alternative embodiment where a horn with a welding profile comprising triangular pyramids in a hexagonal pattern is used, the welding area 21 of the flange 2 shows a regular pattern of triangular depressions 6 as shown in FIG. 7.

The improved ultrasonic welding method and resulting improved stoma systems have two major advantages over the prior art stoma systems. Firstly, the layers can not easily be torn apart. Secondly, due to the pattern of depressions in the welding area 5, 6, the flexibility of the body side wafer 1 with flange 2 is improved.

Summarizing, this patent application concerns a new method of attaching a coupling member (flange) for a stoma system onto the top layer of a body side wafer. In case of a two-piece stoma system the body side adhesive wafer and the pouch are two separate components. Both body side wafer and pouches are provided with a circular coupling member, which allows easy attachment and disconnection of the pouch without disturbing the peristomal skin. The body side wafer preferably consist of a relatively thick skin-friendly hydrocolloid adhesive covered by a polymeric top layer, preferably a polyethylene film. The flange of the body side wafer is also made from plastic—preferably also from polyethylene—and consists of a circular welding area with an upstanding rib as coupling member. The welding area of this flange is much thicker than the polymeric polyethylene top layer of the body side wafer, reason for choosing ultrasonic welding as the most preferable welding method for this purpose. It creates a very easy and reliable seal between the coupling member and the polymeric top layer of the body side flange. The major advantage of a polyethylene film is, that it is a strong material, resistant to aggressive stoma output and easy to weld. A mayor disadvantage is that polyethylene film in the required thickness makes the body side wafer rigid and less flexible. In a preferred embodiment the rigid polyethylene film is replaced by a polyethylene foam layer, which allows the body side wafer to follow the contour of the skin thus enlarging the comfort of the patient. A reliable seal can be obtained in this case by providing the welding surface preferably of the horn with a pattern of projections, preferably with a pattern of linked mini-pyramids, which—when brought ultrasonically into vibration and under relatively high pressure—creates a strong and reliable seal, as each mini-pyramid forces the welding area of the flange to be melted together with the polymeric cell walls of more deeply located layers of foam cells. The resulting secure weld cannot easily be torn apart. A further advantage is also that the pattern of many mini-pyramids in the welding area makes the flange itself much more flexible as well.

It should become apparent to one of ordinary skill in the art that various changes and modifications may be made in the method of the present invention which are within the contemplation of the inventor. Thus, the scope of the present application should not be construed as limited by the specification, drawings thereof, but must be determined from review of the claims included herewith.

For example, also the anvil may be provided with an ultrasonic transducer such that the anvil is preferably vibrated in antiphase with respect to the horn.

For example, the further component may also be a pouch which is welded onto the body side wafer using the method of the invention, resulting in a one-piece stoma system.

The invention claimed is:

1. A method for bonding a body side wafer of an ostomy system and a further component of said ostomy system to each other, comprising the steps of:

welding a body side wafer comprising a layer of polymeric foam to a further component of said ostomy system using an ultrasonic welding apparatus comprising an anvil and a horn, said horn comprising a first welding surface, said anvil comprising a second welding surface, and at least one of the first and second welding surfaces comprising a pattern of projections, the projections comprising a plurality of adjacently placed projections comprising one selected from a group consisting of pyramids, truncated pyramids, prismoids, cones, truncated cones, and cylinders, said welding step comprising the steps of clamping areas to be welded of the body side wafer and the further component between the first and second welding surface, and ultrasonically vibrating said horn with respect to said anvil, wherein, the further component is welded onto said layer of polymeric foam of the body side wafer, and the horn has an inner perimeter, an outer perimeter, a welding profile area defined between the inner and outer perimeters, and the projections are placed adjacent each other along the inner and outer perimeters and fill the welding profile area from the inner perimeter to the outer perimeter.

2. The method of claim 1, wherein, in cross-section, between the inner and outer perimeters, there are plural projections adjacently located.

3. The method of claim 1, wherein, in cross-section, between the inner and outer perimeters, there are at least three projections adjacently located.

4. A method for bonding a body side wafer of an ostomy system and a flange to each other, comprising the steps of:

locating a top polymeric foam layer (11) of a body side wafer (1) proximate to an outwardly projection sealing strip (21) of a flange (2) for coupling to a stoma pouch; and ultrasonically welding the sealing strip (21) onto the top polymeric foam layer by clamping the sealing strip and the top polymeric foam layer between an anvil and a horn, and ultrasonically vibrating one of the horn and the anvil, wherein, the horn has an inner perimeter, an outer perimeter, a welding profile area defined between the inner and outer perimeters, projections are placed adjacent each other along the inner and outer perimeters and fill the welding profile area from the inner perimeter to the outer perimeter, and the projections comprising one selected from a group consisting of pyramids, truncated pyramids, prismoids, cones, truncated cones, and cylinders.

5. The method of claim 4, wherein, in cross-section, between the inner and outer perimeters, there are plural projections adjacently located.

6. The method of claim 5, wherein, in crosssection, between the inner and outer perimeters, there are at least three projections adjacently located.

7. The method of claim 6, wherein, during said welding step the horn is ultrasonically vibrated and pressed under a pressure a range of 70 to 110 PSI.

8. The method of claim 4, wherein, during said welding step, the horn is placed against the sealing strip and the anvil is placed against the top polymeric foam layer.

9. The method of claim 4, wherein, during said welding step, the horn is vibrated.

10. The method of claim 4, wherein, during said welding step, the anvil is vibrated.

11. A method for bonding a body side wafer of an ostomy system and a flange, comprising the steps of:

locating a top polymeric foam layer (11) of a body side wafer against a sealing strip of a pouch coupling flange; and ultrasonically welding the sealing strip to the top polymeric foam layer with the sealing strip and the top polymeric foam layer clamped between an anvil and a horn, wherein, the horn has an inner perimeter, an outer perimeter, a welding profile area defined between the inner and outer perimeters, projections are located adjacent each other around the welding profile area and filling the welding profile area from the inner perimeter to the outer perimeter, and the projections comprise one selected from a group consisting of pyramids, truncated pyramids, prismoids, cones, truncated cones, and cylinders.

12. The method of claim 11, wherein, in cross-section, between the inner and outer perimeters, there are at least three projections adjacently located.

13. The method of claim 12, wherein, during said welding step the horn is ultrasonically vibrated and pressed under a pressure a range of 70 to 110 PSI.

* * * * *